(12) United States Patent
Ausen et al.

(10) Patent No.: US 11,975,469 B2
(45) Date of Patent: May 7, 2024

(54) COEXTRUDED POLYMERIC NETTINGS AND METHOD OF MAKING THE SAME

(71) Applicant: 3M INNOVATIVE PROPERTIES COMPANY, St. Paul, MN (US)

(72) Inventors: Ronald W. Ausen, St. Paul, MN (US); William J. Kopecky, Hudson, WI (US); Michael W. Voigt, Crystal, MN (US); Naimul Karim, Maplewood, MN (US); Vasav Sahni, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 400 days.

(21) Appl. No.: 17/310,666

(22) PCT Filed: Feb. 17, 2020

(86) PCT No.: PCT/IB2020/051313
§ 371 (c)(1),
(2) Date: Aug. 17, 2021

(87) PCT Pub. No.: WO2020/183259
PCT Pub. Date: Sep. 17, 2020

(65) Prior Publication Data
US 2022/0118670 A1    Apr. 21, 2022

Related U.S. Application Data

(60) Provisional application No. 62/816,289, filed on Mar. 11, 2019.

(51) Int. Cl.
*B29C 48/18*        (2019.01)
*B29C 48/00*        (2019.01)
(Continued)

(52) U.S. Cl.
CPC ............ *B29C 48/18* (2019.02); *B29C 48/022* (2019.02); *B29D 28/00* (2013.01); *A61L 15/42* (2013.01);
(Continued)

(58) Field of Classification Search
CPC ..... B29C 48/18; B29C 48/05; B29C 48/3001; B29C 48/345; B29C 48/022; B29D 28/00;
(Continued)

(56) References Cited

U.S. PATENT DOCUMENTS

| 3,498,873 A | 3/1970 | Schrenk |
| 4,634,485 A | 1/1987 | Welygan |

(Continued)

FOREIGN PATENT DOCUMENTS

| WO | WO 2008-148797 | 12/2008 |
| WO | WO 2014-164242 | 10/2014 |
| WO | WO 2015-002730 | 1/2015 |

OTHER PUBLICATIONS

International Search Report for PCT International Application No. PCT/IB2020/051313, mailed on Apr. 21, 2020, 4 pages.

*Primary Examiner* — Nahida Sultana
*Assistant Examiner* — Lawrence D. Hohenbrink, Jr.
(74) *Attorney, Agent, or Firm* — Thomas M. Spielbauer (57) ABSTRACT

Articles comprising first and second coextruded polymeric nettings are described. The articles comprise a plurality of pairs of first segments comprising a first material. Adjacent first segments are joined together via a second segments comprising second material, wherein the second segments extend past the first major surface of each first adjacent segments. The articles further include an adhesive on at least one of the first or second major surfaces of the first segment. The first segments, second segments, and third material each (Continued)

extend continuously for at least 5 mm in the machine direction, and the first and second materials of adjacent pairs are periodically bonded together in the machine direction. A portion of some of the first segments of the first coextruded polymeric netting are engaged between some of the adjacent first segments of the second coextruded polymeric netting.

15 Claims, 9 Drawing Sheets

(51) Int. Cl.
| | |
|---|---|
| *B29D 28/00* | (2006.01) |
| *A61L 15/42* | (2006.01) |
| *A61L 15/58* | (2006.01) |
| *B29C 48/05* | (2019.01) |
| *B29C 48/30* | (2019.01) |
| *B29C 48/345* | (2019.01) |
| *B29K 9/00* | (2006.01) |
| *B32B 3/02* | (2006.01) |
| *B32B 7/12* | (2006.01) |
| *B32B 27/08* | (2006.01) |

(52) U.S. Cl.
CPC ............ *A61L 15/425* (2013.01); *A61L 15/58* (2013.01); *B29C 48/05* (2019.02); *B29C 48/3001* (2019.02); *B29C 48/345* (2019.02); *B29K 2009/00* (2013.01); *B29K 2023/06* (2013.01); *B32B 3/02* (2013.01); *B32B 7/12* (2013.01); *B32B 27/08* (2013.01); *B32B 2459/00* (2013.01); *B32B 2535/00* (2013.01)

(58) Field of Classification Search
CPC ......... B32B 2535/00; B32B 3/02; B32B 7/12; B32B 27/08; B32B 2459/00; B29K 2009/00; B29K 2023/06; A61L 15/42; A61L 15/425; A61L 15/58
USPC ..................................................... 264/173.16
See application file for complete search history.

(56) References Cited

U.S. PATENT DOCUMENTS

| | | | |
|---|---|---|---|
| 4,636,419 | A | 1/1987 | Madsen |
| 4,661,389 | A | 4/1987 | Mudge |
| 5,296,547 | A | 3/1994 | Nestegard |
| 5,393,787 | A | 2/1995 | Nestegard |
| 6,083,856 | A | 7/2000 | Joseph |
| 6,351,420 | B1 | 2/2002 | Akaogi |
| 6,994,904 | B2 | 2/2006 | Joseph |
| 2007/0199654 | A1* | 8/2007 | Kohel ............... B32B 27/12 156/308.2 |
| 2016/0151945 | A1* | 6/2016 | Ausen ............... B29C 43/24 428/131 |
| 2017/0233946 | A1* | 8/2017 | Sealey ............... B32B 5/10 162/111 |

* cited by examiner

COEXTRUDED POLYMERIC NETTINGS AND METHOD OF MAKING THE SAME

CROSS REFERENCE TO RELATED APPLICATIONS

This application is a national stage filing under 35 U.S.C. 371 of PCT/IB2020/051313, filed Feb. 17, 2020, which claims the benefit of U.S. Application No. 62/816,289, filed Mar. 11, 2019, the disclosure of which is incorporated by reference in its/their entirety herein.

BACKGROUND

Coextruded polymeric articles (including layers) having projections are known in the art. For example, it is known to provide a co-extruded, layer structures where the layer is partitioned, not as coextensive layers in the thickness direction, but as stripes or segments along the width dimension of the layer. This has sometimes been called "side-by-side" co-extrusion.

There is a desire for additional polymeric articles with projections that offer different configurations and/or properties (e.g., adhesive properties) over conventional articles. Some adhesive systems that switch from a state of relatively low or no adhesion to a state of much higher adhesion upon application of a certain trigger (commonly called "adhesion on demand" systems) are known. Many of these systems use triggers such as solvents, ultra violet light, heat, or magnetic forces, to create tiered adhesive performance once or repetitively. These systems are limited in applications for several reasons. For many of these triggers, the adhesive system must contain specific chemical groups, which restricts usage to applications where those chemical groups can be tolerated. These systems can be used only where a particular trigger is available and can be effectively applied to the adhesive system. Further, some triggers are difficult or inconvenient for consumers to use. Certain triggers, as well as the chemical groups in the adhesive that respond to such triggers, can be cost-prohibitive.

There is a continuing desire for new coextruded polymeric article constructions. Further, there is a need for "adhesion on demand" systems where the trigger is applicable to all adhesive chemistries, the trigger is more broadly or even universally available, the trigger is easy to apply, not only industrially, but by a consumer, and the adhesion-on-demand system is not exceedingly expensive.

SUMMARY

In one aspect, the present disclosure describes an article comprising first and second coextruded polymeric nettings, the first and second coextruded polymeric nettings each having a machine direction comprising:
a plurality of pairs (in some embodiments, at least 3, 4, 5, 10, 25, 50, 100, 250, 500, 750, or even at least 1000 pairs) of:
first segments each having first and second opposed major surfaces and a thickness, the first segments comprising first material;
second segments comprising second material, wherein adjacent first segments are joined together via a second segment, wherein the second segments extend from the second major surface past the first major surface of each first adjacent segment and has a distal end, the second segments having first and second opposed major surfaces, wherein there is a gap between adjacent second segments; and
a third material comprising adhesive, different from the first and second materials on at least one the first or second major surfaces (in some embodiments, on both the first and second major surfaces) of at least every other (in some embodiments, on each) first segment,
wherein the first segments, second segments, and third material each extend continuously for at least 5 mm (in some embodiments, at least 10 mm, 25 mm, 50 mm, 1 cm, 5 cm, 10 cm, 50 cm, 75 cm, 1 m, 5 m, 10 m, 25 m, 50 m, 100 m, 500 m, or even at least 1000 m) in the machine direction, and wherein first and second materials of adjacent pairs are periodically bonded together in the machine direction, wherein a portion of some of the first segments of the first coextruded polymeric netting are engaged between some of the adjacent first segments of the second coextruded polymeric netting. "Different" as used herein means at least one of (a) a difference of at least 2% in at least one infrared peak, (b) a difference of at least 2% in at least one nuclear magnetic resonance peak, (c) a difference of at least 2% in the number average molecular weight, or (d) a difference of at least 5% in polydispersity. Examples of differences in polymeric materials that can provide the difference between polymeric materials include composition, microstructure, color, and refractive index. The term "same" in terms of polymeric materials means not different.

In some embodiments, the first segment has first and second opposed major surfaces, wherein the second segment extends past both the first and second surfaces of the first segment.

Netting described herein are useful, for example, for tape landing zones (e.g., in medical applications where the netting is wrapped around an appendage and attached to itself to provide a medical tape landing zone without adhesion to skin), bundling applications where it is desired to maintain breathability without an air tight barrier such as what happens with elastomeric thin film wraps, and bundling applications where it is desired to have compression wrap without adhesion to the wrapped substrate.

DETAILED DESCRIPTION

Figure 1:
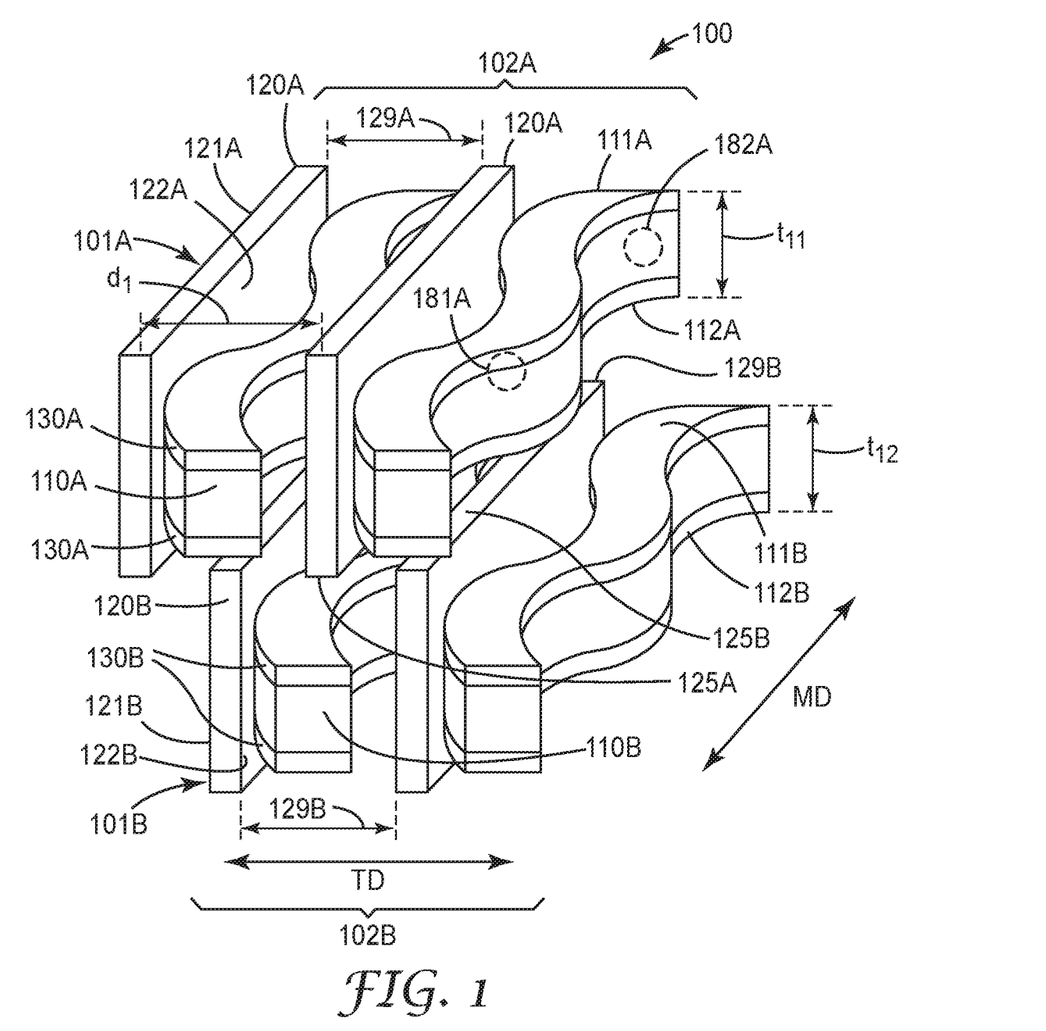
FIG. 1 is a schematic cross-sectional view of an exemplary article described herein.
Figure 1A:
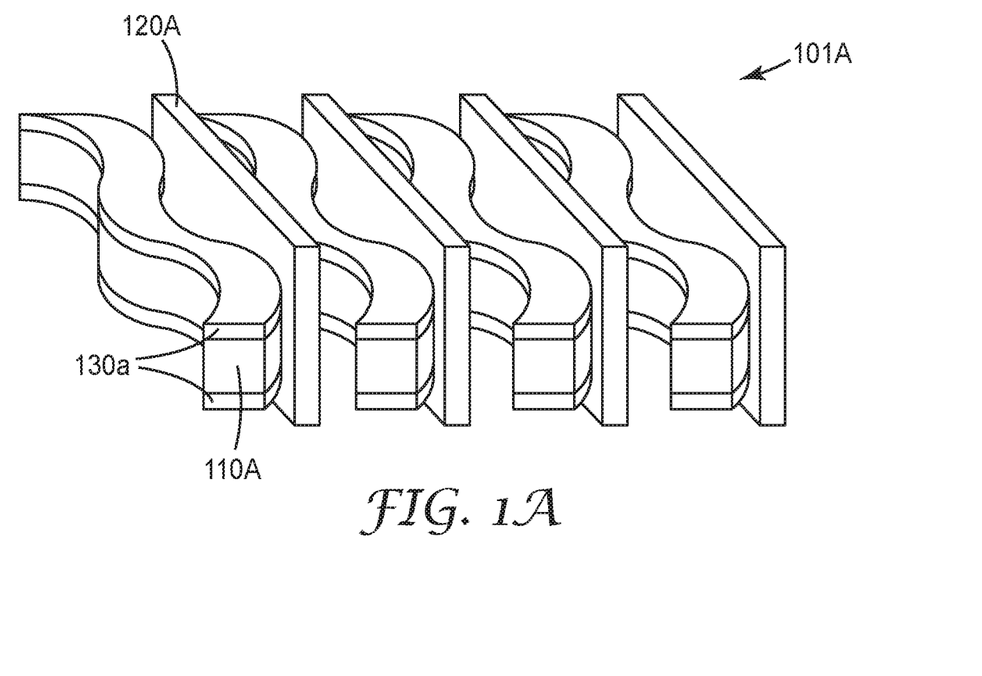
FIG. 1A is an individual netting used to form the article of FIG. 1.

Referring to FIGS. 1 and 1A, exemplary article described herein 100 comprises first and second coextruded polymeric nettings 101A and 101B each have machine direction MD and a transverse direction TD. First and second coextruded polymeric nettings 101A, 101B, respectively, comprise plurality of pairs 102A, 102B, respectively, of first segments 110A, 110B, respectively, comprise first material, second segments 120A, 120B, respectively, each comprise second material, and third material 130A, 130B, respectively comprising adhesive, different from the first and second materials. First segments 110A, 110B, respectively, each have first and second opposed major surfaces 111A, 112A, 111B, 112B, respectively, and thickness $t_{11}$, $t_{12}$, respectively. Adjacent first segments 110A, 110B, respectively, are joined together via second segment 120A, 120B, respectively. Second segments 120A, 120B, respectively extend from second major surface 112A, 112B, respectively, past first major surface 111A, 111B, respectively of each first adjacent segment 110A, 110B, respectively, and has distal end 125A, 125B, respectively. Second segments 120A, 120B, respectively, have first and second opposed major surfaces 121A, 122A, and 121B, and 122B respectively. There is gap 129A, 129B, respectively, between adjacent second segments 120A, 120B, respectively. Third material 130A, 130B, respectively, is on at least one of first or second major surfaces 111A, 112A, 111B, 112B, respectively (as shown on both the first and second major surfaces 111A, 112A, 111B, 112B, respectively) of at least every other (as shown on each) first segment 110A, 110B, respectively. First segments 110A, 110B, respectively, second segments 120A, 120B, respectively, and third material 130A, 130B, respectively, each extend continuously for at least 5 mm. First and second materials of adjacent pairs 101A, 101B, respectively, are periodically bonded together in machine direction MD. Distance $d_1$ is the repeating distance between second segments and can be used to calculate the second segments per centimeter. Region 11 with demarcation between adhesive and second segments is shown as reference 181A. Region 21 without demarcation is shown as reference 182A.

In some embodiments, there is a demarcation line between the first and second segments that is parallel to the segments, known as a bond region. Bonds are formed when two adjacent molten polymer segments collide with each other. Adjacent segments are extruded at alternating speeds such that adjacent molten segments continually collide, forming bonds, and then part, forming the net openings. Segments are extruded in the same direction, and thus, these bonds are parallel bonds, all formed in the same direction. The bonds are in the same plane, they do not cross over each other. For a given segment there is a first segment on one side which intermittently bonds, and a second segment on the opposite side which is also intermittently bonded. Bond regions are continuations of the two segments, and thus the bond region comprises the sum of the two adjacent segments. Typically, segments continue without disconnect and can be followed continuously through the bond regions. In some embodiments, there is also a demarcation line between the adhesive and the first segments. These constructions can be formed by methods described herein where materials are coextruded in a manner that results in a distinct line of orientation visible at the polymer boundary between connected segments and protrusions. This demarcation line or boundary region between connected segments and protrusions can be detected using Differential Scanning Calorimetry. Comparing by temperature modulated differential scanning calorimetry a region containing mostly a demarcation line (e.g., in FIG. 1, Region 1 181A) versus a region that does not substantially contain material from the demarcation line (in FIG. 1, Region 2 182A) a difference in heat flow/heat capacity is observed that is believed to be consistent with an energy release or reduction in molecular orientation/internal stress. That is, although not wanting to be bound by theory, it is believed that the thermal signatures of the regions may be a combination of material thermal transitions and the material response to retained thermal/processing history.

FIG. 1 shows precise alignment of second segments within the gaps of the mating second segments. In practice precise alignment is not required. The second segments prevent generally planar surfaces from contacting the adhesive. The narrowness of the second segments enables them to continuously, or in some embodiments, intermittently bond to the adhesive of the first segment. The result of this construction is an adhesive tape which is very breathable, because it is a net, and is also not sticky, because adhesive generally does not contact the generally planar surfaces.

In some embodiments, the first and second materials are at least one of a thermoplastic resin (e.g., at least one of, including copolymers and blends thereof, a polyolefin (e.g., polypropylene and polyethylene), a polyvinyl chloride, a polystyrene, a nylon, a polyester (e.g., polyethylene terephthalate) or an elastomer (e.g., an ABA block copolymer, a polyurethane, a polyolefin elastomer, a polyurethane elastomer, a metallocene polyolefin elastomer, a polyamide elastomer, an ethylene vinyl acetate elastomer, and a polyester elastomer)). Selection of the thermoplastic resin typically depends on the selection of the adhesive used as the third material. The thermoplastic resin is generally processed at similar conditions as the adhesive (e.g., temperature and viscosity). When articles described herein are used in medical applications (e.g., as a wrap around an appendage), it can be desirable for the article to be sufficiently transparent or translucent to view or generally view the skin under the wrap. Materials that may provide such transparent or translucent articles include thermoplastic elastomers that are essentially non-crystalline (e.g., ethylene vinyl acetate copolymers, polyurethane, polyolefin copolymers, and styrenic block copolymers).

In some embodiments, the segments are within the same plane.

In some embodiments, a portion of the first major surface of the first segment between second segments is free of adhesive.

In some embodiments, the second segments are generally parallel to each other and generally perpendicular to the first major surface of the adjacent first segments.

In some embodiments, the first and second are the same material and different from the third material.

In some embodiments, the first, second, and third materials are different from each other.

In some embodiments, the second segments have a height from the first major surface of the adjacent segment to the distal ends of the second segments are in a range from 0.05 to 5 (in some embodiments, in a range from 0.1 to 2, or even 0.1 to 1) mm.

In some embodiments, the second segments have a longest cross-sectional dimension in a range from 0.05 to 0.5 (in some embodiments, in a range from 0.05 to 0.2, or even 0.05 to 0.1) mm.

In some embodiments, the second segments have an aspect ratio (i.e., height from the first major surface of the adjacent first segment to width) of at least 1.5:1 (in some embodiments, at least 2:1, 3:1, or even at least 4:1).

In some embodiments, the first segments are spaced apart not more than 5 mm (in some embodiments, not more than 1 mm).

In some embodiments, there is a distance between the first and second major surfaces of the first segments in a range from 0.025 mm to 1 mm (in some embodiments, in a range from 0.025 mm to 0.5 mm, 0.025 mm to 0.2 mm, or even 0.025 mm to 0.1 mm).

In some embodiments, there are at least 2.5 (in some embodiments, at least 5, 10, 15, 20, 25, 30, 35, or even up to 40) second segments per cm.

In some embodiments, the third material has a thickness in a range from 0.001 to 0.25 (in some embodiments, in a range from 0.001 to 0.1, 0.001 to 0.05, 0.001 to 0.025, or even 0.001 to 0.01) mm.

In some embodiments, the adhesive is at least one of an acrylate copolymer pressure sensitive adhesive, a rubber-based adhesive (e.g., those based on at least one of natural rubber, polyisobutylene, polybutadiene, butyl rubber, or styrene block copolymer rubber), a silicone polyurea-based adhesive, a silicone polyoxamide-based adhesive, a polyurethane-based adhesive, or a poly(vinyl ethyl ether)-based adhesive. In some embodiments, the styrene block copolymer rubber is of the form as described in the U.S. Pat. No. 5,296,547 (Nestegard et al.) and U.S. Pat. No. 5,393,787 (Nestegard et al.).

Adhesives at melt and shear rate conditions within the die typically result in low relatively viscosity. A viscosity mismatch of adhesive to first segment material may result in encapsulation of adhesive around the first segment. Therefore, matching the viscosity of the first and materials may be desirable. In some embodiments, the first and third materials are within a melt viscosity ratio of about 1:1 or 10:1 (in some embodiments, at most 3:1). Greater differences in viscosity may require less contact between first and third materials within the die. For large viscosity ratio pairs, it may be desirable for the demarcation line between the first and third material be formed outside the die.

In some embodiments, the adhesive is on at least one of the first and second major surfaces of each second segment.

In some embodiments, a portion of the major surface adjacent to the respective distal end of the second segments are free of the adhesive.

In some embodiments, the distal ends of at least some (in some embodiments, all) of the second segments are free of adhesive.

In another aspect, the present disclosure describes a method of making the first and second coextruded polymeric netting, the method comprising:

providing an extrusion die comprising of at least three cavities, a dispensing surface, and fluid passageways between the at least three cavities and the dispensing surface, wherein the dispensing surface has an array of first dispensing orifices separated by an array of second dispensing orifices, wherein the first and second dispensing orifices each have a height and a width, wherein the second dispensing orifices each have a height to width aspect ratio of at 1.5:1, and wherein the height of the second dispensing orifices is at least two times larger than the height of the first dispensing orifices, and wherein the first dispensing orifices comprise a plurality of a repeating sequence of shims that together provide a fluid passageway between the third and first cavities and the first orifice; and wherein the second dispensing orifices comprises a plurality of a repeating sequence of shims that together provide a passageway between the second cavity and the second orifice;

dispensing polymeric ribbons from the second dispensing orifices at a first speed while simultaneously dispensing polymeric segments from the first dispensing orifices at a second speed to provide the polymeric netting, wherein the second speed is at least twice the first speed.

Coextruded polymeric articles described herein (including that shown in FIG. 1), each of the segments and adhesive portions may be considered monolithic (i.e., having a generally uniform composition) and are not fibrous. This is accomplished by formation of weld lines, called demarcation lines at the die region where the dispensing orifices merge together at the distal opening. Further, the segments and the adhesive are not nonwoven materials, nor are they coated or added via as a secondary step. In some embodiments described below, however, portions of the articles may be apertured. Typically, the segments and adhesive are co-extruded and melt bonded together to form coextruded, continuous, polymeric articles. Referring again to FIG. 1, coextruded polymeric nettings 101A, 101B can be prepared, for example, by extrusion from a die having a variety of passageways from cavities within the die to a dispensing slot, including exemplary dies described herein (see, e.g., FIG. 9). The die may conveniently be comprised of a plurality of shims. In some embodiments the first dispensing orifices comprise a plurality of a repeating sequence of shims that together provide a fluid passageway between the third and first cavities and the first orifice; and wherein the second dispensing orifices comprises a plurality of a repeating sequence of shims that together provide a passageway between the second cavity and the second orifice.

In some embodiments, the shims will be assembled according to a plan that provides a sequence of shims of diverse types. Since different applications may have different requirements, the sequences can have diverse numbers of shims. The sequence may be a repeating sequence that is not limited to a particular number of repeats in a particular zone. Or the sequence may not regularly repeat, but different sequences of shims may be used. The shape of the passageways within, for example, a sequence of shims, may be identical or different. Examples of passageway cross-sectional shapes include round, square, and rectangular shapes. In some embodiments, the shims that provide a passageway between one cavity and the dispensing orifice might have a flow restriction compared to the shims that provide a passageway between another cavity and a dispensing orifice.

Individual cavities and passageways provide a conduit for polymer to orifices to create the segments and adhesive portions. The second segment material flow streams merge together to form a continuous, solid coextruded polymeric article, at the die orifice portion of the die. Spacer shims separate the first and second orifices.

In some embodiments, extrusion dies described herein include a pair of end blocks for supporting the plurality of shims. In these embodiments, it may be convenient for one, or even all, of the shims to each have at least one through-holes for the passage of connectors between the pair of end blocks. Bolts disposed within such through-holes are one convenient approach for assembling the shims to the end blocks, although the ordinary artisan may perceive other alternatives for assembling the extrusion die. In some embodiments, the at least one end block has an inlet port for introduction of fluid material into one, or more, of the cavities.

In some embodiments, the shims will be assembled according to a plan that provides a repeating sequence of shims of diverse types. The repeating sequence can have diverse numbers of shims per repeat. For a first example, a repeating sequence comprised of three different shims is described below to create the orifice pattern shown in FIG. 2 to create the coextruded polymeric article 101A shown in FIG. 1A. When the three-shim repeating sequence is properly provided with molten polymer, it extrudes a continuous netting via the first and second plurality of orifices.

In some embodiments, the assembled shims (conveniently bolted between the end blocks) further comprise a manifold body for supporting the shims. The manifold body has at least one (e.g., in some embodiments, at least two three, four, or more) manifold therein, the manifold having an outlet. An expansion seal (e.g., made of copper or alloys thereof) is disposed to seal the manifold body and the shims, such that the expansion seal defines a portion of at least one of the cavities (in some embodiments, a portion of both the first and second cavities), and such that the expansion seal allows a conduit between the manifold and the cavity.

Typically, the passageway between cavity and dispensing orifice is up to 25 mm in length. Sometimes the fluid passageways leading to one array has greater fluid restriction than the fluid passageways leading to one or more of the other arrays. Typically, the combined passageway for the first and third material is up to 5 mm in length. The combined passageway may need to be shortened, and in some embodiments eliminated, dependent upon the viscosity ratio of the first and third materials.

The shims for dies described herein typically have thicknesses in the range from 50 micrometers to 125 micrometers, although thicknesses outside of this range may also be useful. Typically, the fluid passageways have thicknesses in a range from 50 micrometers to 750 micrometers, and lengths less than 25 mm (with generally a preference for smaller lengths for decreasingly smaller passageway thicknesses), although thicknesses and lengths outside of these ranges may also be useful. For large diameter fluid passageways, several smaller thickness shims may be stacked together, or single shims of the desired passageway width may be used.

The shims are tightly compressed to prevent gaps between the shims and polymer leakage. For example, 12 mm (0.5 inch) diameter bolts are typically used and tightened, at the extrusion temperature, to their recommended torque rating. Also, the shims are aligned to provide uniform extrusion out the extrusion orifice, as misalignment can lead to segments extruding at an angle out of the die which inhibits desired bonding of the net. To aid in alignment, an alignment key can be cut into the shims. Also, a vibrating table can be useful to provide a smooth surface alignment of the extrusion tip.

In practicing methods described herein, the polymeric materials might be solidified simply by cooling. This can be conveniently accomplished passively by ambient air, or actively, for example, by quenching the extruded first and second polymeric materials on a chilled surface (e.g., a chilled roll). In some embodiments, any of the first, second, third or fourth polymeric materials are low molecular weight polymers that need to be cross-linked to be solidified, which can be done, for example, by electromagnetic or particle radiation. In some embodiments, it is desirable to maximize the quenching time to increase the bond strength.

Figure 2:
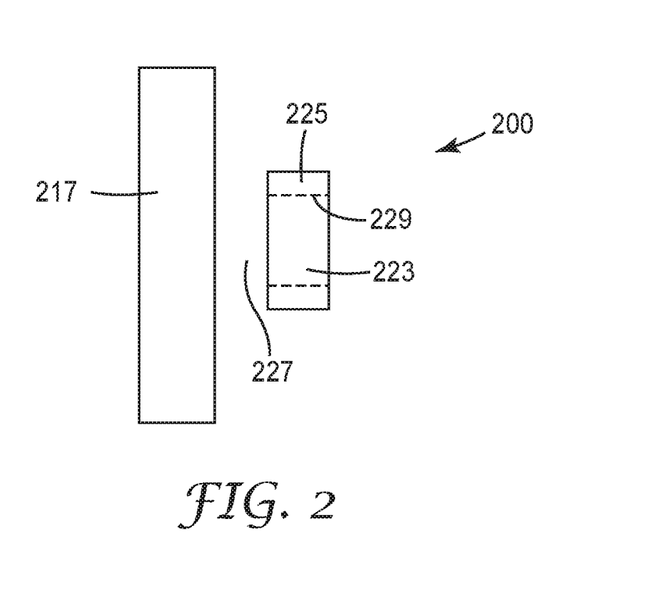
FIG. 2 is a schematic cross-sectional view of an exemplary die extrusion orifice pattern at the dispensing surface of the die employed in the formation of an exemplary coextruded polymeric article described herein.

FIG. 2 is a schematic view of the dispensing surface of an extrusion die employed in the formation of an exemplary coextruded polymeric article described herein. Orifice plan 200 shows first orifices 223, and second orifices 217. As will be described in detail later, the orifices are spaced apart to provide passageway sidewalls between passageways. The individual flowstreams of the first segment merge together to form a single and continuous segment from the first orifice. The demarcation lines are created within the first orifice where the first and third materials meet, a relatively short distance from the dispensing surface of the die. Typically, the molten adhesives have a lower viscosity than the viscosity of the thermoplastic polymers. Therefore, it may be desirable to minimize the common land length of the region in the die where the third and first material are joined together; otherwise encapsulation of the first segment with the third material may occur. The latter may result in the first and second segments weakly bonding together, or not bonding together. Bond regions are formed between the first and second segment with spacing 227. The velocity mismatch of the two segments and the orifice spacing enables creation of repeating bonds between segments to form netting.

Figure 3A:
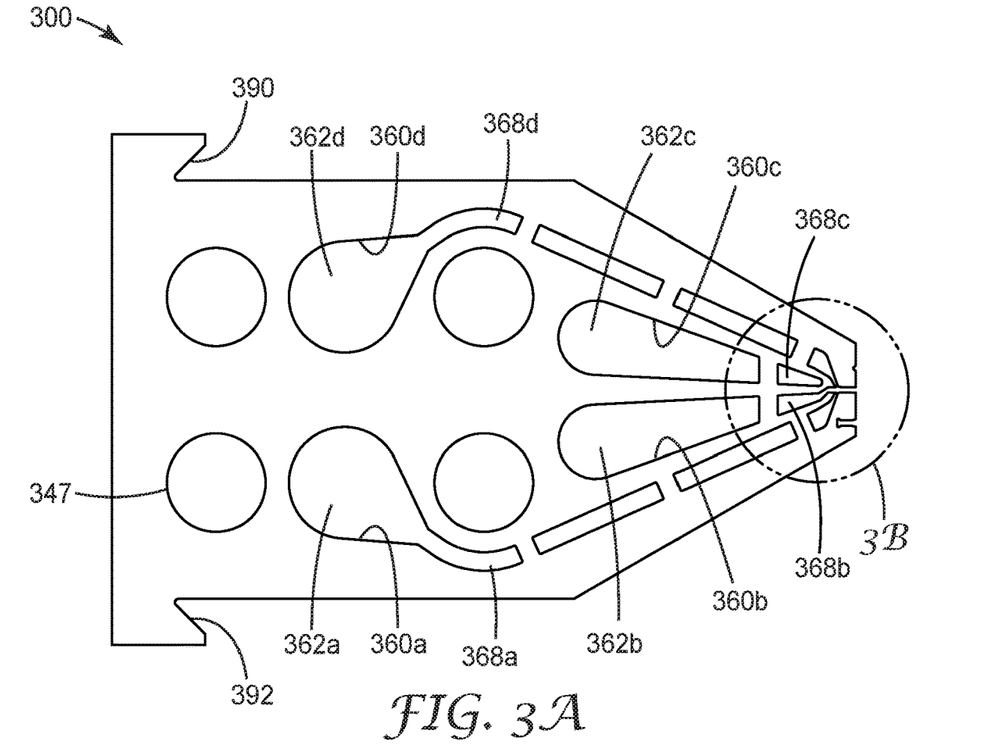
FIG. 3A is a plan view of an exemplary embodiment of a shim suited to form a sequence of shims capable of forming an exemplary coextruded polymeric article, for example, as shown in the schematic cross-sectional views of FIG. 1A.
Figure 3B:
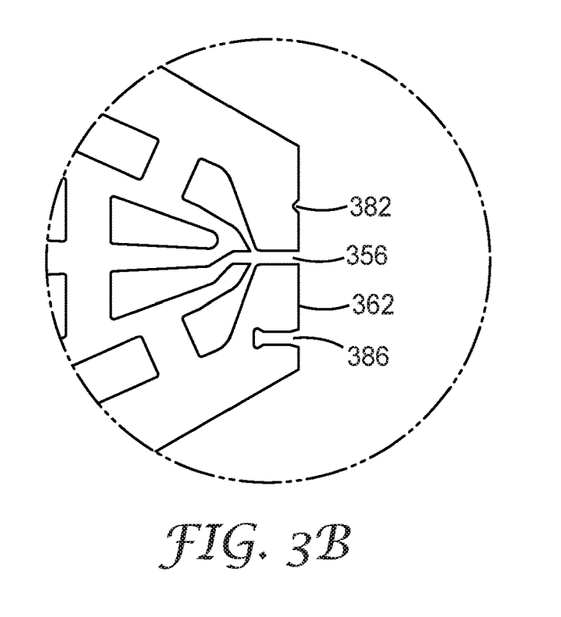
FIG. 3B is an expanded region near the dispensing surface of the shim shown in FIG. 3A.
Figure 6:
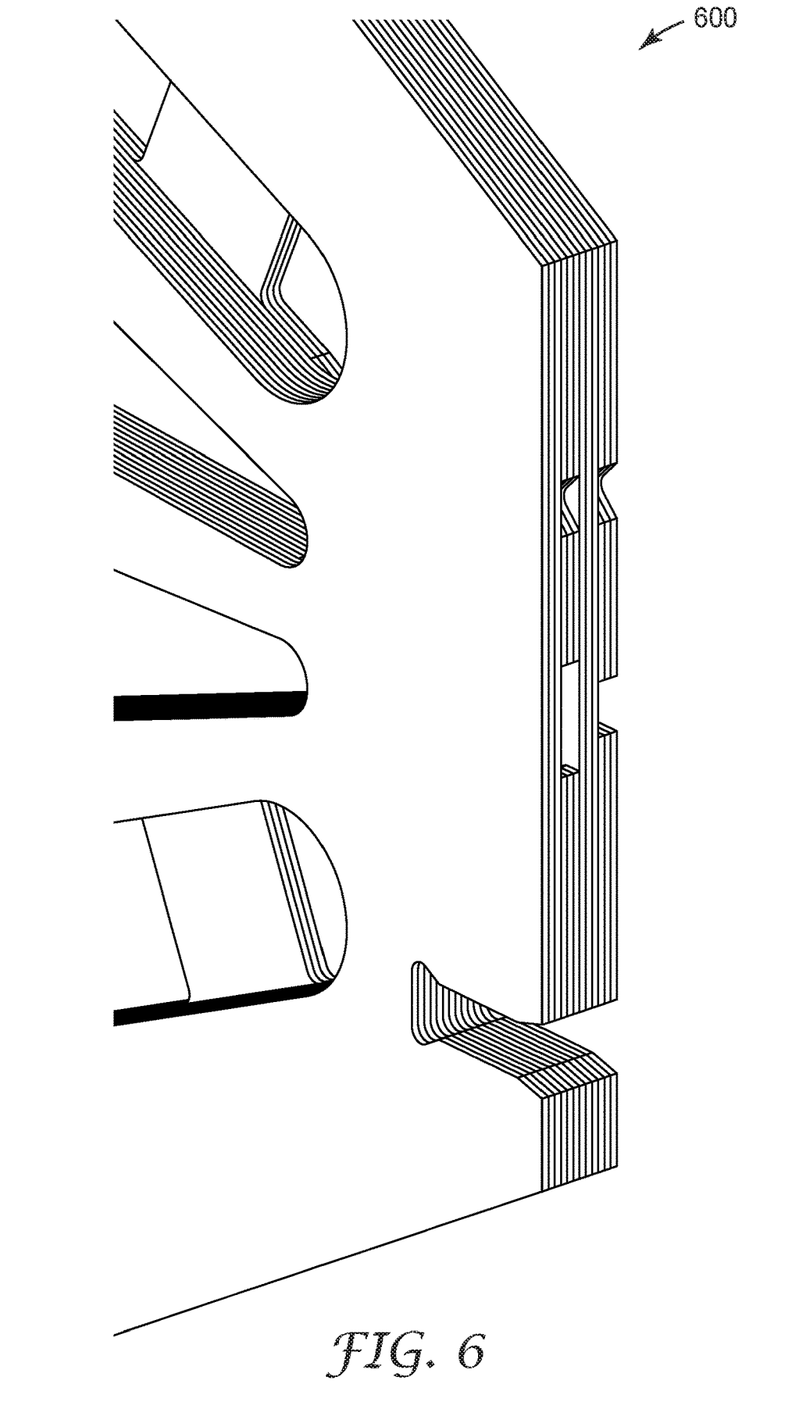
FIG. 6 is a perspective assembly drawing of several different exemplary sequences of shims employing the shims of FIGS. 3A, 4A, and 5A for making exemplary coextruded polymeric articles described herein, segments and protrusions in a repeating arrangement as shown in FIG. 1A.
Figure 7:
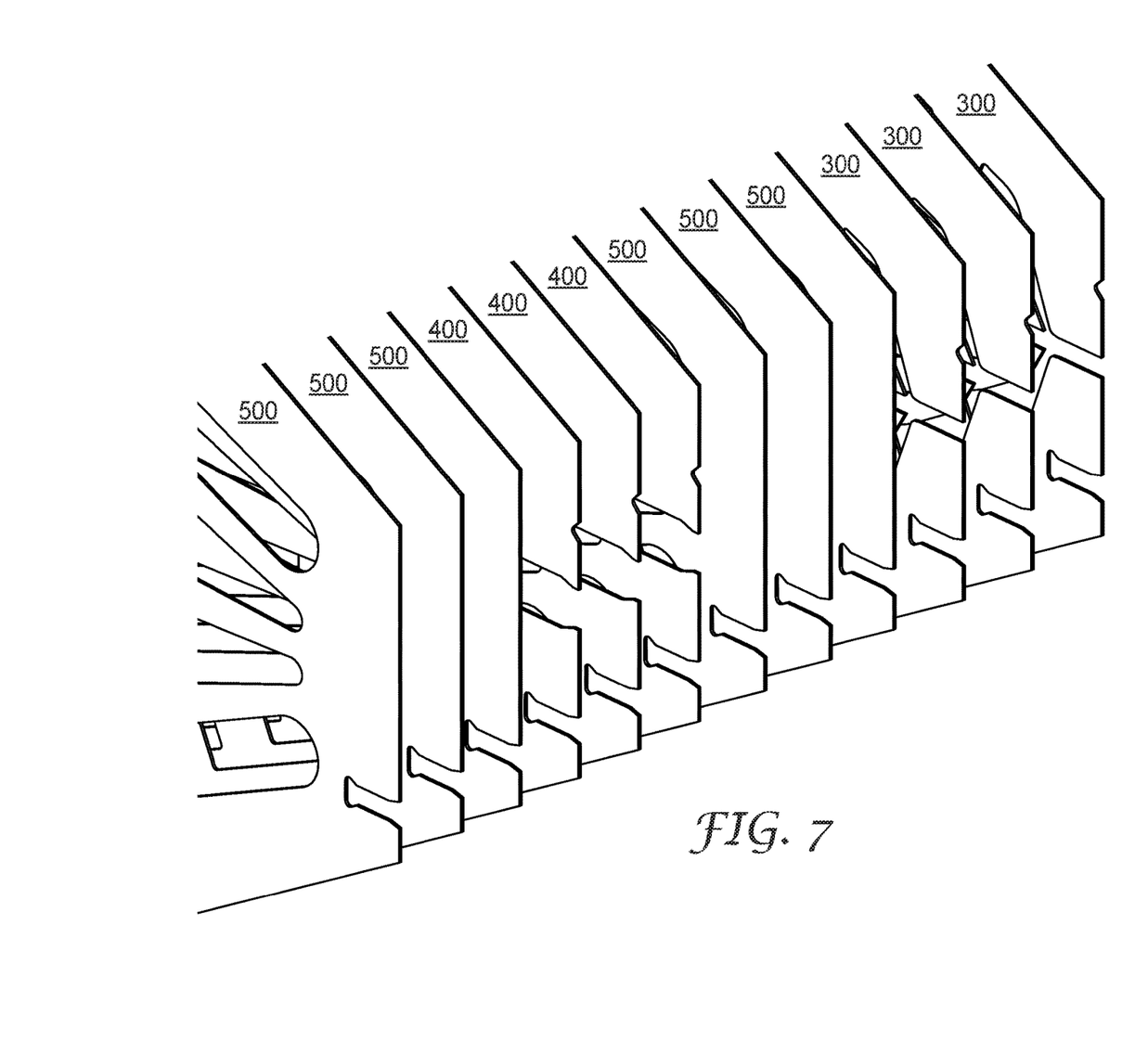
FIG. 7 is a perspective view of the some of the sequence of shims of FIG. 6, further exploded to reveal some individual shims.

Referring now to FIGS. 3A and 3B, a plan view of shim 300 is illustrated. Shim 300 has first aperture 360a, second aperture 360b third aperture 360c, and fourth aperture 360d. When shim 300 is assembled with others as shown in FIGS. 6 and 7, aperture 360a aids in defining first cavity 362a, aperture 360b aids in defining second cavity 362b, aperture 360c aids in defining third cavity 362c, and aperture 360d aids in defining third cavity 362d. Passageways 368a, 368b, 368c, and 368d cooperate with analogous passageways on adjacent shims to allow passage from cavities 362a, 362b, 362c, and 362d to the dispensing surfaces of the appropriate shims when the shims are assembled as shown in FIGS. 6 and 7.

Shim 300 has several holes 347 to allow the passage of, for example, bolts, to hold shim 300 and others to be described below into an assembly. Shim 300 also has dispensing surface 362, and in this embodiment, dispensing surface 362 has indexing groove 386 which can receive an appropriately shaped key to ease assembling diverse shims into a die. The shim may also have identification notch 382 to help verify that the die has been assembled in the desired manner. This embodiment has shoulders 390 and 392 which can assist in mounting the assembled die with a mount of the type shown in FIG. 9. Shim 300 has dispensing opening 356, in dispensing surface 362. Dispensing opening 356 may be more clearly seen in the expanded view shown in FIG. 3B. Dispensing opening 356 has connection to cavity 362a, 362b, and 362d. It might seem that there is no path from cavity 362a to dispensing opening 356, via, for example, passageway 368a, but the flow has a route in the perpendicular-to-the-plane-of-the-drawing dimension when the sequence of shims is completely assembled. The same is true for passageway 368b and 368d. Shim 300 creates a portion of the first segment, with adhesive layers on the first and second major surface.

Figure 4A:
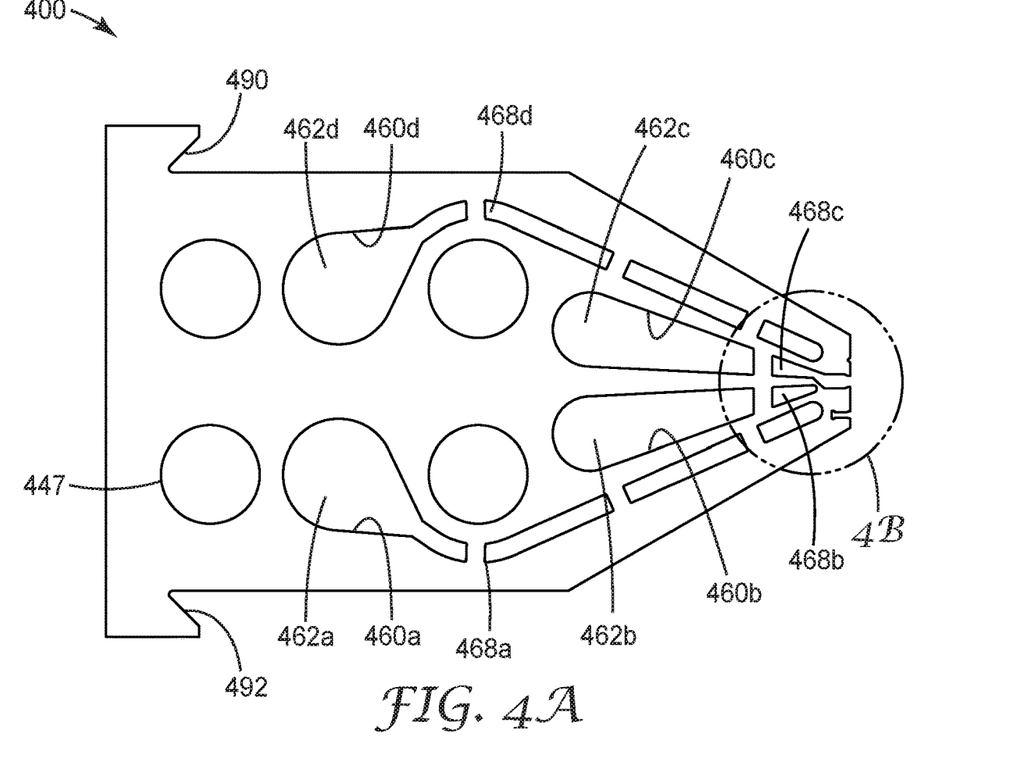
FIG. 4A is a plan view of an exemplary embodiment of a shim suited to form a sequence of shims capable of forming a coextruded polymeric article, for example, as shown in the schematic cross-sectional views of FIG. 1A.
Figure 4B:
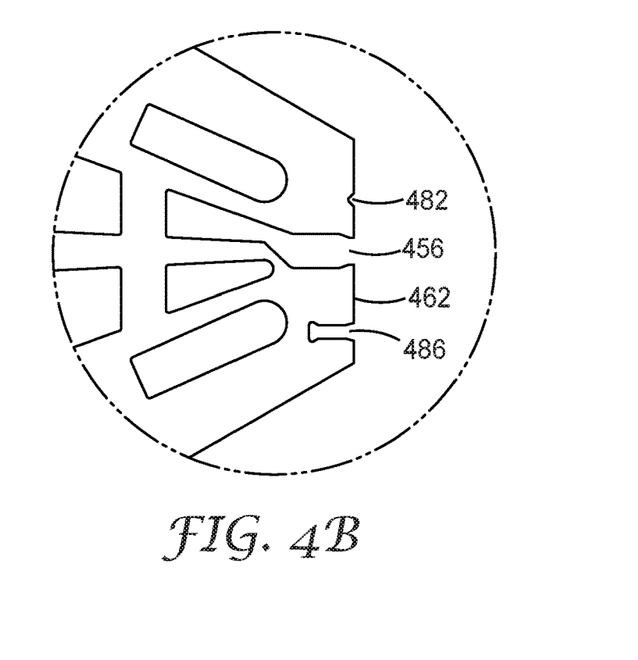
FIG. 4B is an expanded region near the dispensing surface of the shim shown in FIG. 4A.

Referring to FIGS. 4A, and 4B, a plan view of shim 400 is illustrated. Shim 400 has first aperture 460a, second aperture 460b, third aperture 460c, and fourth aperture 460d. When shim 400 is assembled with others as shown in FIGS. 6 and 7, aperture 460a aids in defining first cavity 462a, aperture 460b aids in defining second cavity 462b, aperture 460c aids in defining third cavity 462c, and aperture 460d aids in defining third cavity 462d. Passageways 468a, 468b, 468c, and 468d cooperate with analogous passageways on adjacent shims to allow passage from cavities 462a, 462b, 462c, and 462d to the dispensing surfaces of the appropriate shims when the shims are assembled as shown in FIGS. 6 and 7.

Shim 400 has several holes 447 to allow the passage of, for example, bolts, to hold shim 400 and others to be described below into an assembly. Shim 400 also has dispensing surface 462, and in this embodiment, dispensing surface 462 has indexing groove 486 which can receive an appropriately shaped key to ease assembling diverse shims into a die. The shim may also have identification notch 482 to help verify that the die has been assembled in the desired manner. This embodiment has shoulders 490 and 492 which can assist in mounting the assembled die with a mount of the type shown in FIG. 9. Shim 400 has dispensing opening 456, in dispensing surface 462. Dispensing opening 456 may be more clearly seen in the expanded view shown in FIG. 4B. Dispensing opening 456 has connection to cavity 462c. It might seem that there is no path from cavity 462c to dispensing opening 456, via, for example, passageway 468c, but the flow has a route in the perpendicular-to-the-plane-of-the-drawing dimension when the sequence of shims is completely assembled. Shim 400 creates a portion of the second segment.

Figure 5A:
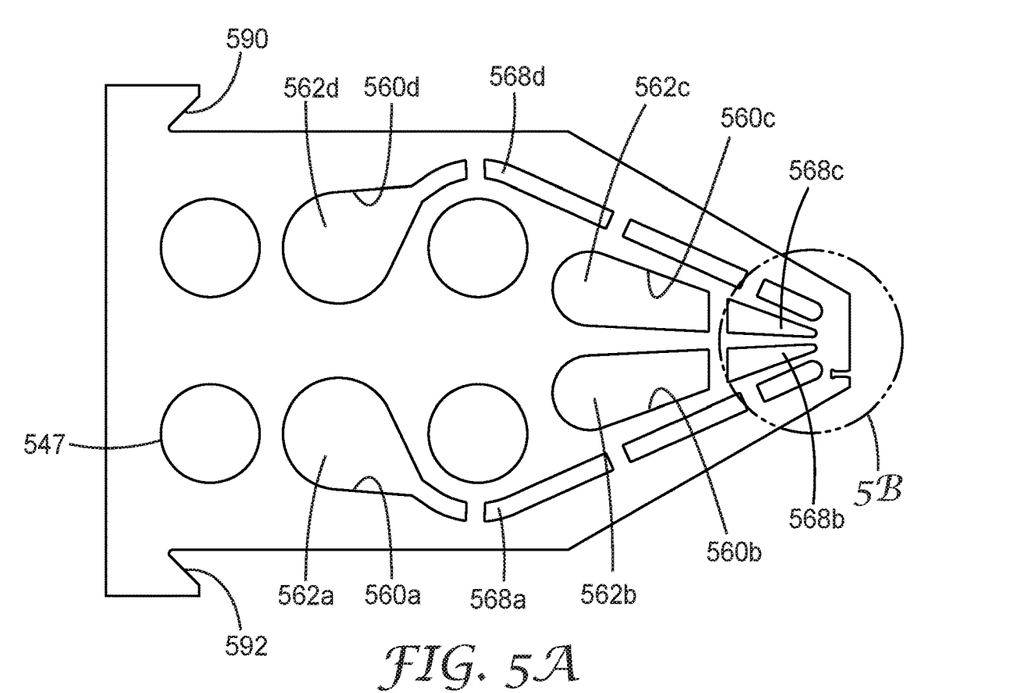
FIG. 5A is a plan view of an exemplary embodiment of a shim suited to form a sequence of shims capable of forming a coextruded polymeric article, for example, as shown in the schematic cross-sectional views of FIG. 1A.
Figure 5B:
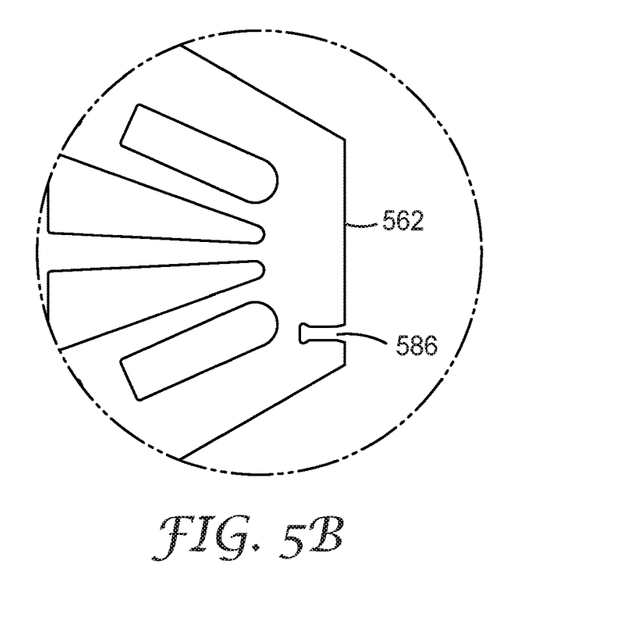
FIG. 5B is an expanded region near the dispensing surface of the shim shown in FIG. 5A.

Referring to FIGS. 5A and 5B, a plan view of shim 500 is illustrated. Shim 500 has first aperture 560a, second aperture 560b, third aperture 560c, and fourth aperture 560d. When shim 500 is assembled with others as shown in FIGS. 6 and 7, aperture 560a aids in defining first cavity 562a, aperture 560b aids in defining second cavity 562b, aperture 560c aids in defining third cavity 562c, and aperture 560d aids in defining third cavity 562d. Passageways 568a, 568b, 568c, and 568d cooperate with analogous passageways on adjacent shims to allow passage from cavities 562a, 562b, 562c, and 562d to the dispensing surfaces of the appropriate shims when the shims are assembled as shown in FIGS. 6 and 7.

Shim 500 has several holes 547 to allow the passage of, for example, bolts, to hold shim 500 and others to be described below into an assembly. Shim 500 also has dispensing surface 562, and in this embodiment, dispensing surface 562 has indexing groove 586 which can receive an appropriately shaped key to ease assembling diverse shims into a die. This embodiment has shoulders 590 and 592 which can assist in mounting the assembled die with a mount of the type shown in FIG. 9. Shim 500 does not have a dispensing opening. It creates the space between segment orifices and forms the demarcation lines between segments in the bond areas.

Referring to FIG. 6, a perspective assembly drawing of several different repeating sequences of shims, collectively 600, employing the shims of FIGS. 3-5 to produce coextruded polymeric article 100 shown in FIG. 1 is shown. The dispensing surface has two orifices that form the first and second segment. The passageways forming the layers within the first segment (not shown). When a complete die is assembled, typically many repeats of this shim sequence are collectively assembled to form a netting of the first and second segments.

Referring to FIG. 7, an exploded perspective assembly drawing of a repeating sequence of shims employing the shims of FIGS. 3-5 is illustrated. In the illustrated embodiment, the repeating sequence includes, from bottom to top as the drawing is oriented, three instances of shim 300 which forms the first segment, three instances of shim 500 which forms the space between orifices, three instances of shim 400 which forms the second segment, and three instances of shim 500 which again forms the space between orifices.

Figure 8:
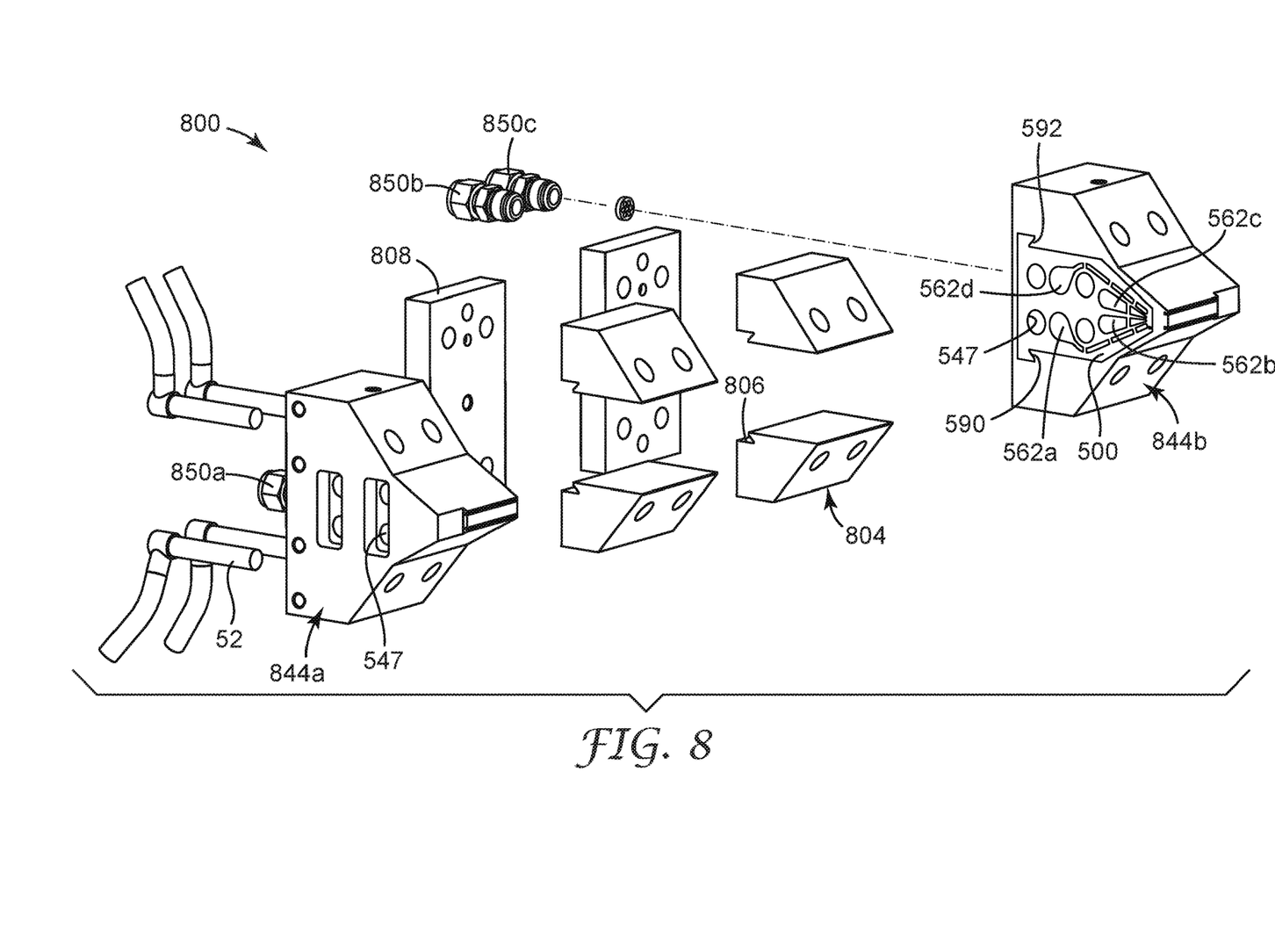
FIG. 8 is an exploded perspective view of an example of a mount suitable for an extrusion die composed of multiple repeats of the sequence of shims of FIG. 6.

Referring to FIG. 8, an exploded perspective view of a mount 800 suitable for an extrusion die composed of multiple repeats of the repeating sequence of shims of FIGS. 6 and 7 is illustrated. Mount 800 is particularly adapted to use shims 300, 400, and 500 as shown in FIGS. 6 and 7. For visual clarity, however, only a single instance of shims is shown in FIG. 8. The multiple repeats of the repeating sequence of shims are compressed between two end blocks 844a and 844b. Conveniently, through bolts can be used to assemble the shims to end blocks 844a and 844b, passing through holes 547 in shims 500 et al.

In this embodiment, inlet fittings 850a, 850b, 850c, and a fourth fitting not shown provide a flow path for up to four streams of molten polymer through end blocks 844a and 844b to cavities 562a, 562b, and 562c, and 562d. Compression blocks 804 have notch 806 that conveniently engages the shoulders on shims (e.g., 590 and 592) on 500. When mount 800 is completely assembled, compression blocks 804 are attached by, for example, machine bolts to backplates 808. Holes are conveniently provided in the assembly for the insertion of cartridge heaters 52.

Figure 9:
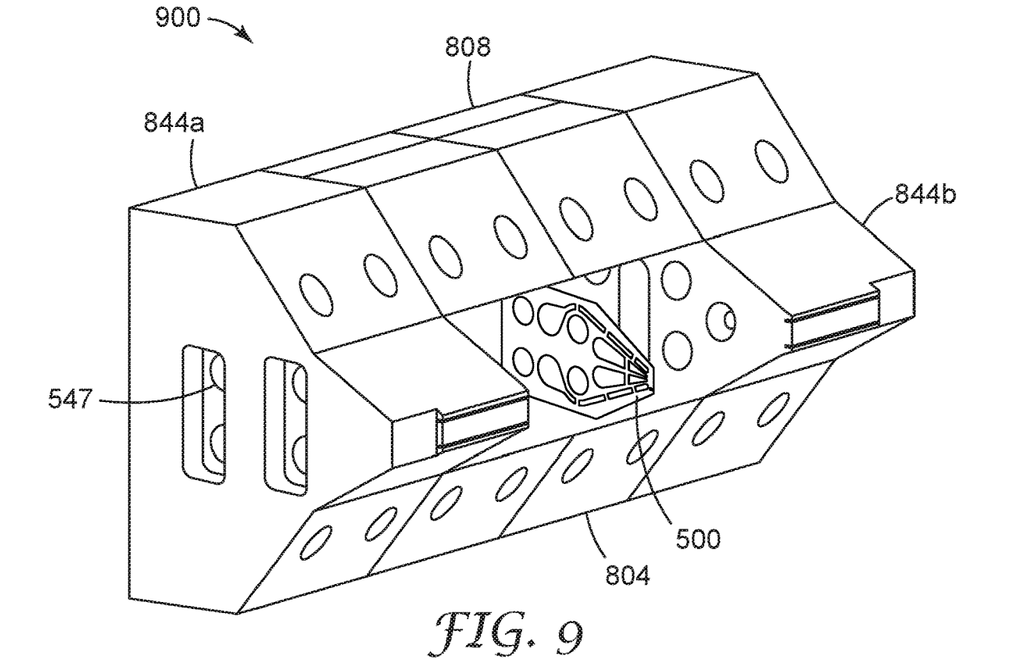
FIG. 9 is a perspective view of the mount of FIG. 8 in an assembled state.

Referring to FIG. 9, a perspective view of the mount 900 of FIG. 8 is illustrated in a partially assembled state. A few shims, for example, 500 are in their assembled positions to show how they fit within mount 800, but most of the shims that would make up an assembled die have been omitted for visual clarity.

In some embodiments, polymeric materials used to make coextruded polymeric articles described herein may comprise a colorant (e.g., pigment and/or dye) for functional (e.g., optical effects) and/or aesthetic purposes (e.g., each has different color/shade). Suitable colorants are those known in the art for use in various polymeric materials. Exemplary colors imparted by the colorant include white, black, red, pink, orange, yellow, green, aqua, purple, and blue. In some embodiments, it is desirable level to have a certain degree of opacity for one or more of the polymeric materials. The amount of colorant(s) to be used in specific embodiments can be readily determined by those skilled in the (e.g., to achieve desired color, tone, opacity, transmissivity, etc.). If desired, the polymeric materials may be formulated to have the same or different colors.

Netting described herein are useful, for example, for tape landing zones (e.g., in medical applications where the netting is wrapped around an appendage and attached to itself to provide a medical tape landing zone without adhesion to skin), bundling applications where it is desired to maintain breathability without an air tight barrier such as what happens with elastomeric thin film wraps (i.e., the netting construction of the articles described herein facilitates the breathability of the article), and bundling applications where it is desired to have compression wrap without adhesion to the wrapped substrate.

EXEMPLARY EMBODIMENTS

1A. An article comprising first and second coextruded polymeric nettings, the first and second coextruded polymeric nettings each having a machine direction comprising:
   a plurality of pairs (in some embodiments, at least 3, 4, 5, 10, 25, 50, 100, 250, 500, 750, or even at least 1000 pairs) of:
      first segments each having first and second opposed major surfaces and a thickness, the first segments comprising first material;
      second segments comprising second material, wherein adjacent first segments are joined together via a second segment, wherein the second segments extend from the second major surface past the first major surface of each first adjacent segment and has a distal end, the second segments having first and second opposed major surfaces, wherein there is a gap between adjacent second segments; and
      a third material comprising adhesive, different from the first and second materials on at least one the first or second major surfaces (in some embodiments, on both the first and second major surfaces) of at least every other (in some embodiments, on each) first segment,
   wherein the first segments, second segments, and third material each extend continuously for at least 5 mm (in some embodiments, at least 10 mm, 25 mm, 50 mm, 1 cm, 5 cm, 10 cm, 50 cm, 75 cm, 1 m, 5 m, 10 m, 25 m, 50 m, 100 m, 500 m, or even at least 1000 m) in the machine direction, and wherein first and second materials of adjacent pairs are periodically bonded together in the machine direction, wherein a portion of some of the first segments of the first coextruded polymeric netting are engaged between some of the adjacent first segments of the second coextruded polymeric netting.

2A. The article of Exemplary Embodiment 1A, wherein the segments are within the same plane.

3A. The article of any preceding A Exemplary Embodiment, wherein the adhesive is at least one of an acrylate copolymer pressure sensitive adhesive, a rubber-based adhesive (e.g., those based on at least one of natural rubber, polyisobutylene, polybutadiene, butyl rubber, or styrene block copolymer rubber), a silicone polyurea-based adhesive, a silicone polyoxamide-based adhesive, a polyurethane-based adhesive, or a poly(vinyl ethyl ether)-based adhesive.

4A. The article of any of preceding A Exemplary Embodiment, wherein, a portion of the major surface adjacent to the respective distal end of the second segments are free of the adhesive.

5A. The article of any preceding A Exemplary Embodiment, wherein the distal ends of at least some (in some embodiments, all) of the second segments are free of adhesive.

6A. The article of any preceding A Exemplary Embodiment, wherein there is a demarcation line between the first and second segments that is parallel to the segments.

7A. The article of any preceding A Exemplary Embodiment, wherein the second segments are generally parallel to each other and generally perpendicular to the first major surface of the adjacent first segments.

8A. The article of any preceding A Exemplary Embodiment, wherein the first segments comprise first material, the second segments comprise second material, and the adhesive comprises third material, wherein the first and second are the same material and different from the third material.

9A. The article of any preceding A Exemplary Embodiment, wherein the first segments comprise first material and the second segments comprise second material, wherein the first, second, and third materials are different from each other.

10A. The article of any preceding A Exemplary Embodiment, wherein the first and second materials are at least one of a thermoplastic resin (e.g., at least one of, including copolymers and blends thereof, a polyolefin (e.g., polypropylene and polyethylene), a polyvinyl chloride, a polystyrene, a nylon, a polyester (e.g., polyethylene terephthalate) or an elastomer (e.g., an ABA block copolymer, a polyurethane, a polyolefin elastomer, a polyurethane elastomer, a metallocene polyolefin elastomer, a polyamide elastomer, an ethylene vinyl acetate elastomer, and a polyester elastomer)).

11A. The article of any preceding A Exemplary Embodiment, wherein the second segments have a height from the first major surface of the adjacent segment to the distal end is in a range from 0.05 to 5 (in some embodiments, in a range from 0.1 to 2, or even 0.1 to 1) mm.

12A. The article of any preceding A Exemplary Embodiment, wherein the second segments have a longest cross-sectional dimension in a range from 0.05 to 0.5 (in some embodiments, in a range from 0.05 to 0.2, or even 0.05 to 0.1) mm.

13A. The article of any preceding A Exemplary Embodiment, wherein the second segments have an aspect ratio (i.e., height from the first major surface of the adjacent first segment to width) of at least 1.5:1 (in some embodiments, at least 2:1, 3:1, or even at least 4:1).

14A. The article of any preceding A Exemplary Embodiment, wherein the first segments are spaced apart not more than 5 mm (in some embodiments, not more than 1 mm).

15A. The article of any preceding A Exemplary Embodiment having a distance between the first and second major surfaces of the first segments are in a range from 0.025 mm to 1 mm (in some embodiments, in a range from 0.025 mm to 0.5 mm, 0.025 mm to 0.2 mm, or even 0.025 mm to 0.1 mm).

16A. The article of any preceding A Exemplary Embodiment, wherein there are at least 2.5 (in some embodiments, at least 5, 10, 15, 20, 25, 30, 35, or even up to 40) second segments per cm.

17A. The article of any preceding A Exemplary Embodiment, wherein the third material has a thickness in a range from 0.001 to 0.25 (in some embodiments, in a range from 0.001 to 0.1, 0.001 to 0.05, 0.001 to 0.025, or even 0.001 to 0.01) mm.

Advantages and embodiments of this invention are further illustrated by the following example, but the particular materials and amounts thereof recited in this example, as well as other conditions and details, should not be construed to unduly limit this invention. All parts and percentages are by weight unless otherwise indicated.

Example A co-extrusion die as generally shown in FIG. 9 and assembled with a multi shim repeating pattern of extrusion orifices as generally shown in FIGS. 6 and 7, was prepared. The thickness of the shims in the repeat sequence was 4 mils (0.102 mm). These shims were formed from stainless steel, with perforations cut by a wire electron discharge machining. The shims were stacked in a repeating sequence was 300, 300, 300, 500, 500, 500, 400, 400, 400, 500, 500, 500. This configuration creates a repeating length of 48 mils (1.22 mm) with cavities, passageways and orifices such that the first extruder feeds the center of the orifices for the first segment, the second extruder feeds the top and bottom of the orifices for the first segment, and the third extruder feeds the orifices for the second segment. The shims were assembled to create a die at approximately 6 cm in width. The extrusion orifices were aligned in a collinear, alternating arrangement, and resulting dispensing surface as shown in FIG. 2.

The inlet fittings on the two end blocks were each connected to three conventional extruders. The extruders feeding the first and third cavity were loaded with polyethylene (obtained under the trade designation "ELVAX 3170" from Dow Chemical, Midland, MI). The extruder feeding the second cavity was a 25 mm twin screw extruder, used to compound an elastomer with tackifier adhesive formulation. A 1:1 ratio of tackifier to elastomer was compounded continuously and fed through a gear pump and then connected to the second cavity of the die. The elastomer was a styrene block copolymer the styrene block copolymer rubber (obtained under the trade designation "KRATON 1340" from Kraton Polymers, Houston, TX). The tackifier was a hydrocarbon tackifier, (obtained under the trade designation "SUKOREZ 210" from Kolon Industries, Cardiff by the Sea, CA).

The melt was extruded vertically into an extrusion quench takeaway. The quench roll was a smooth temperature-controlled chrome plated 20 cm diameter steel roll. The quench nip temperature was controlled with internal water flow. The web path wrapped 180 degrees around the chrome steel roll and then to a windup roll. Under these conditions a polymeric layer was extruded.

Other process conditions are listed below:

| | |
|---|---|
| Flow rate for the first cavity | 1.4 kg/hr. |
| Flow rate for the second cavity | 0.45 kg/hr. |
| Flow rate for the third cavity | 2.7 kg/hr. |
| Extrusion temperature | 190° C. |
| Quench roll temperature | 10° C. |
| Quench takeaway speed | 6.2 m/min. |

Figure 10:
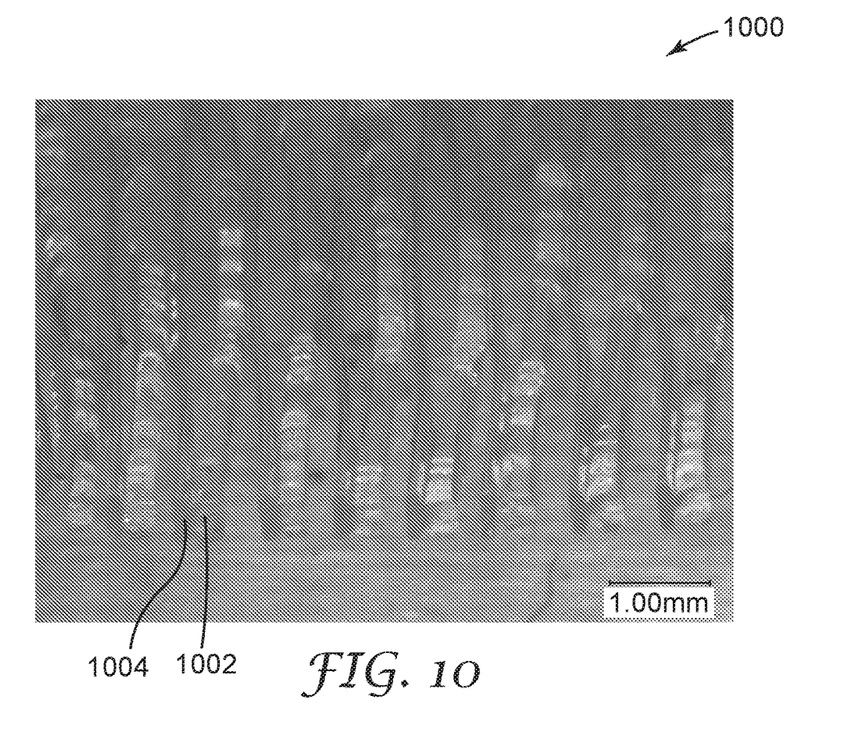
FIG. 10 is an optical image of the Example article.

An optical microscope was used to measure web dimensions. A digital optical image of Example netting 100 is shown in FIG. 10. Netting 1000 includes first segments 1002 and second segments 1004.

| | |
|---|---|
| First segment width: | 0.3 mm |
| First segment height: | 0.52 mm |
| Second segment width: | 0.15 mm |
| Second segment height: | 0.61 mm |
| Machine direction bond repeat | 6 mm |
| Machine direction bond length | 2 mm |

Foreseeable modifications and alterations of this disclosure will be apparent to those skilled in the art without departing from the scope and spirit of this invention. This invention should not be restricted to the embodiments that are set forth in this application for illustrative purposes.

What is claimed is:

1. An article comprising first and second coextruded polymeric nettings, the first and second coextruded polymeric nettings each having a machine direction comprising:
   a plurality of pairs of:
      first segments each having first and second opposed major surfaces and a thickness, the first segments comprising first material;
      second segments comprising second material, wherein adjacent first segments are joined together via a second segment, wherein the second segments extend from the second major surface past the first major surface of each first adjacent segment and a distal end, the second segments having first and second opposed major surfaces, wherein there is a gap between adjacent second segments; and
      a third material comprising adhesive, different from the first and second materials on at least one of the first or second major surfaces of the first segment,
   wherein the first segments, second segments, and third material each extend continuously for at least 5 mm in the machine direction, and wherein first and second materials of adjacent pairs are periodically bonded together in the machine direction,
   wherein a portion of some of the first segments of the first coextruded polymeric netting are engaged between some of the adjacent first segments of the second coextruded polymeric netting.

2. The article of claim 1, wherein the segments are within the same plane.

3. The article of claim 1, wherein the adhesive is at least one of an acrylate copolymer pressure sensitive adhesive, a rubber-based adhesive (e.g., those based on at least one of natural rubber, polyisobutylene, polybutadiene, butyl rubber, or styrene block copolymer rubber), a silicone polyurea-based adhesive, a silicone polyoxamide-based adhesive, a polyurethane-based adhesive, or a poly(vinyl ethyl ether)-based adhesive.

4. The article of claim 1, wherein there is a demarcation line between the first and second segments that is parallel to the segments.

5. The article of claim 1, wherein the second segments are generally parallel to each other and generally perpendicular to the first major surface of the adjacent first segments.

6. The article of claim 1, wherein the first segments comprise first material, the second segments comprise second material, and the adhesive comprises third material, wherein the first and second are the same material and different from the third material.

7. The article of claim 1, wherein the first segments comprise first material and the second segments comprise second material, wherein the first, second, and third materials are different from each other.

8. The article of claim 1, wherein the first and second materials are at least one of a thermoplastic resin.

9. The article of claim 1, wherein the second segments have a height from the first major surface of the adjacent segment to the distal end is in a range from 0.05 to 5 mm.

10. The article of claim 1, wherein the second segments have a longest cross-sectional dimension in a range from 0.05 to 0.5 mm.

11. The article of claim 1, wherein the second segments have an aspect ratio of at least 1.5:1.

12. The article of claim 1, wherein the first segments are spaced apart not more than 5 mm.

13. The article of claim 1 having a distance between the first and second major surfaces of the first segments are in a range from 0.025 mm to 1 mm.

14. The article of claim 1, wherein there are at least 2.5 second segments per cm.

15. The article of claim 1, wherein the third material has a thickness in a range from 0.001 to 0.25 mm.

* * * * *